United States Patent
Siepmann

[19]

[11] Patent Number: 6,114,172
[45] Date of Patent: Sep. 5, 2000

[54] PROCESS AND DEVICE FOR DETERMINING THE BIOLOGICAL OXYGEN DEMAND OF SEWAGE

[75] Inventor: Friedrich W. Siepmann, Gross-Umstadt, Germany

[73] Assignee: Isco Inc., Lincoln, Nebr.

[21] Appl. No.: 09/051,543

[22] PCT Filed: Sep. 18, 1996

[86] PCT No.: PCT/EP96/04083

§ 371 Date: Jul. 9, 1998

§ 102(e) Date: Jul. 9, 1998

[87] PCT Pub. No.: WO97/14960

PCT Pub. Date: Apr. 24, 1997

[30]       Foreign Application Priority Data

Oct. 13, 1995 [DE] Germany .......................... 195 38 180

[51] Int. Cl.[7] .............................. G01N 33/18; C12M 1/34
[52] U.S. Cl. .......................... 436/62; 435/30; 435/287.1; 435/287.5; 435/817; 422/79
[58] Field of Search .................... 435/29, 31, 30, 435/287.1, 287.4, 287.5, 817; 422/79; 436/62

[56]              References Cited

U.S. PATENT DOCUMENTS 3,510,406   5/1970   Stack .
4,073,692   2/1978   Ciaccio et al. .
4,314,969   2/1982   Arthur et al. .
4,350,763   9/1982   Suzuki et al. .
4,650,767   3/1987   Arthur .
4,748,127   5/1988   Siepmann et al. .
5,085,759   2/1992   Harker .

FOREIGN PATENT DOCUMENTS 24 15 771   10/1975   Germany .................................. 436/62
30 04 855    8/1981   Germany .................................. 422/79
32 21 966   12/1983   Germany .

*Primary Examiner*—William H. Beisner
*Attorney, Agent, or Firm*—Burns, Doane, Swecker & Mathis, L.L.P.

[57]              ABSTRACT

In order to determine the biological oxygen demand of sewage, a sample of sewage is taken into a reaction vessel in which there is a biological bath which is kept moving turbulently by an agitator. An oxygen probe measure the oxygen consumption per unit time. After each measuring cycle the reaction vessel is rinsed with diluting water and is then ready for another measuring cycle. The reaction vessel penetrates into the sewage to be tested. The sewage sample enters the reaction vessel via an aperture.

9 Claims, 1 Drawing Sheet

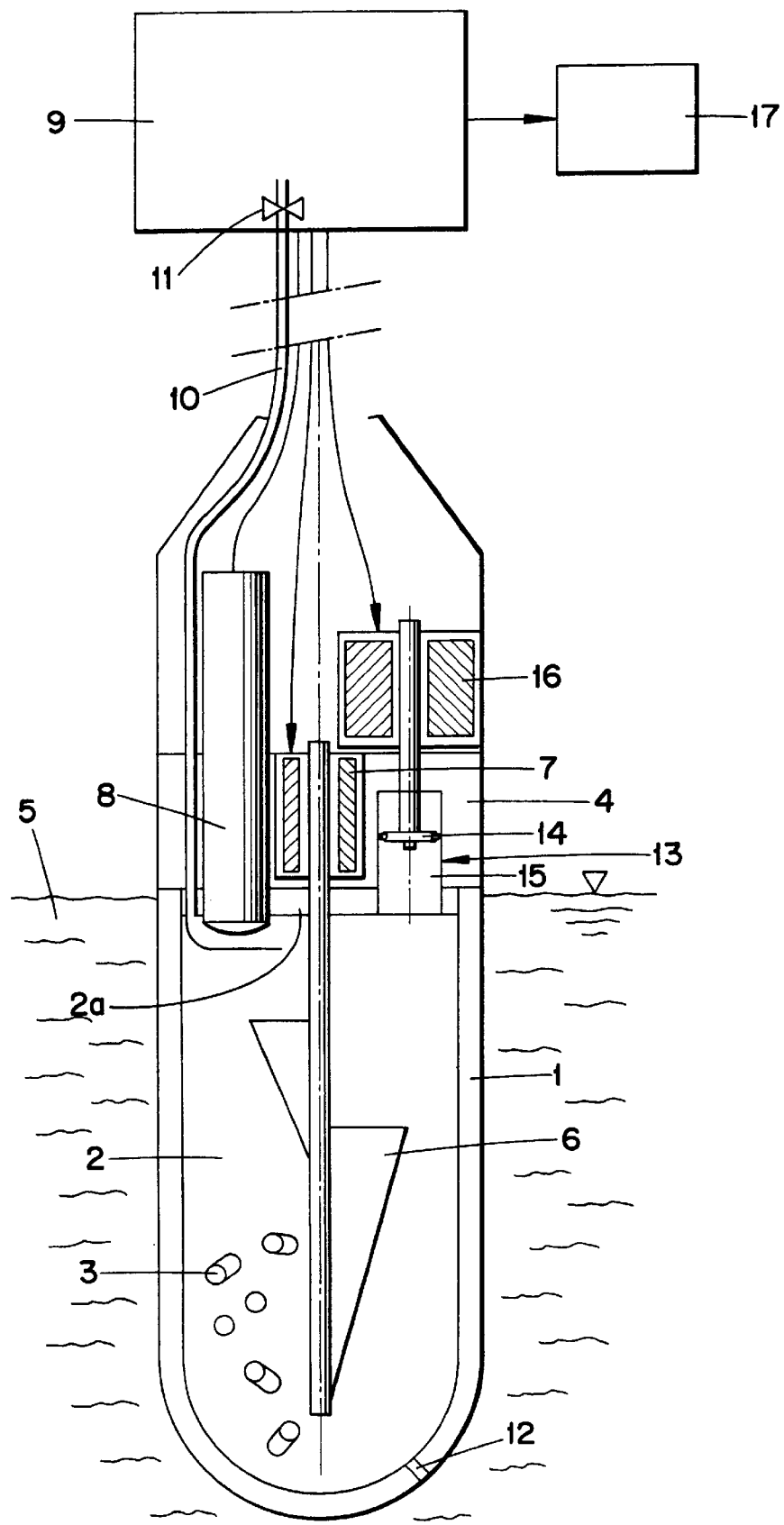

PROCESS AND DEVICE FOR DETERMINING THE BIOLOGICAL OXYGEN DEMAND OF SEWAGE

BACKGROUND OF THE INVENTION

The invention concerns a process to determine the biological oxygen demand (BOD) of sewage, whereby a sewage sample is mixed with a biologically neutral dilution water at a predetermined degree of dilution and the oxygen concentration is measured in a biological bath which changes as a result of the biological reaction of the predetermined bio-mass with the diluted sewage sample in the biological bath.

The biological oxygen demand (BOD) represents an important parameter to indicate the degree of filth in sewage, because the filth loading of sewage predominantly depends on biologically degradable substances. The common idea in the known processes to determine this degree of filth is that a bio-mass, consisting of aerobic micro-organisms usually placed on a growth surface, is nourished in a biological bath with the sewage to be evaluated or a dilution thereof. The oxygen consumption occurring as a result of the biological reaction leads to a diminishment of the oxygen concentration in the biological bath which is measured and drawn to determine the biological oxygen demand and thus the degree of filth of the sewage to be analyzed.

In a known process of the type named at the beginning (EP-B-0 049 887) which, in contrast to the previously known, time-consuming processes, brought a basic improvement and acceleration of BOD determination, a sample stream of the sewage to be evaluated was diluted before its continuous entry into the biological bath by means of the constantly measured introduction of dilution water at a predetermined degree of dilution. The oxygen concentration was measured before entry into the biological bath and after its exit from the biological bath. The average measured value was kept constant at a predetermined value by changing the degree of dilution. This degree of dilution serves to determine the biological oxygen demand. The turbulent circulation of the bio-mass in the biological bath, which is required for a satisfactory reaction speed, occurs by means of the continuous pumping in a loop of the fluid contained in the biological bath.

The device required for the conduct of this process is relatively complicated, because a regulated amount of the sample stream and the dilution water is required. Measurement of the oxygen must occur at two locations. An additional pump is required to pump the fluid out of the biological bath.

It is therefore the task of this invention to so formulate a process of the type named at the outset, that it can be performed simply, quickly and with little requirement for equipment.

SUMMARY OF THE INVENTION

The task of the invention is solved by a predetermined amount of a sewage sample being added to a biological bath filled with oxygen-saturated dilution water and intermittently mixed, so that the controlling oxygen consumption per unit of time can be measured and the biological bath can be rinsed with dilution water.

This process is intermittently performed and, after calibration of the operating conditions by means of one or more measurement cycles, results in a measured value for the biological oxygen demand in the sewage evaluated during each individual measuring cycle.

The necessary requirement for fluids limits itself in the process of this invention to one sewage sample being brought into the biological bath during each measurement cycle and the bath being rinsed with dilution water after each measurement until the content of the biological bath with respect to biologically degradable matter is so small that it can be discounted. Since the dilution water is hereby introduced in a non-proportioned manner, no pump is necessary; a mere connection to a water line will suffice. For the proportioned addition of an amount of sewage, a very simple, intermittently operating positive displacement pump will suffice. The process can therefore be performed quickly and simply with very little equipment needs, whereby a satisfactorily high degree of measurement can be achieved.

In a favored execution model of the invention it is envisioned, that a constant degree of dilution can be regulated during each process cycle by means of the addition of a constant amount of the sewage sample and that the biological oxygen demand will be determined from the oxygen consumption per unit of time and the degree of dilution. The constant degree of dilution is achieved in a very simple manner, in that during each process cycle a constant amount of sewage sample is introduced into the biological bath.

Instead of that, it is also possible in each process cycle to so proportion the amount of the sewage sample, that a predetermined constant oxygen consumption per unit of time is regulated in the biological bath and that from the currently selected degree of dilution the biological oxygen demand can be determined.

The invention involves an advantageous device to perform a process. Proceeding from a known device (EP-B 0 049 887) with a reaction vessel containing the biological bath, a proportioning device for the sewage sample, an introductory device for the dilution water, a device to determine the oxygen concentration in the biological bath, and a circulation device for the biological bath, the device of the invention is thereby characterized by the reaction vessel being a closed container into which a feeder line for the dilution water empties, by the device to determine the oxygen demand per unit of time manifesting an oxygen probe placed in the reaction vessel, and by the reaction vessel being connected to the sewage to be measured by means of an opening which serves as an entrance opening for the sewage sample and as an exit opening when rinsing the biological bath.

Lines which carry sewage and thus can become dirty are completely absent here. This system through which fluids do flow consists basically only of a reaction vessel, which as a result of the biological reactions taking place therein and the rinsing procedure, can operate largely free of maintenance.

In a favored execution model it is envisioned, that the reaction vessel forms a probe head that can be dipped into the sewage to be evaluated. The device takes up only a small amount of space and can be brought to various measuring locations in a simple manner, whereby it is only necessary to lower the probe head into the sewage to be evaluated.

All essential devices required for the measuring process can be combined in a probe base to which the reaction vessel shaped as a probe head is attached. The measuring probe thus formed, which can be lowered into the sewage to be evaluated, need only be connected to a central station, at which evaluation equipment is located, by means of a water line for the dilution water and an electric line for pump and agitator operation, as well as measurement and control connections.

BRIEF DESCRIPTION OF THE DRAWINGS

In the following section execution models of the invention are described in more detail based on a drawing. The drawing shows in a simplified fashion a device to determine the biological oxygen demand of sewage, whereby the measurement probe is shown in a longitudinal view.

DETAILED DESCRIPTION OF A PREFERRED EMBODIMENT OF THE INVENTION

In a basically closed, cylindrical, long, reaction vessel 1 there is a biological bath 2 containing a freely movable growth body 3.

The growth body 3 which, for example, can be constructed as a hollow cylinder manifests growth surfaces for aerobic micro-organisms which form a bio-mass. The biomass is capable of decomposing bio-degradable materials by consuming the oxygen released.

The reaction vessel 1 is placed in a sealed manner on a probe base 4 and is dipped into the sewage to be evaluated in order to perform the measurement.

The shaft of an agitator 6 which is powered by an electric motor 7 is positioned in the probe base 4 and constantly agitates the biological bath 2. The agitator 6 which extends into the reaction vessel 1 thus represents a circulation device for the biological bath 2.

A oxygen probe 8 is positioned in the probe base 4 and measures the oxygen consumption per unit of time in the biological bath 2 and furnishes that measured value to a central control device 9. Oxygen-saturated dilution water can be introduced into the reaction vessel 1 by means of a water line 10 in which a valve activated by the control device is located. The water line 10 passes through an immobile wall 2a situated opposite to, and facing, an opening 12.

In its lower portion the reaction vessel 1 manifests the opening 12 which serves as the entry opening for the sewage sample and as the exit opening during the rinsing of the biological bath 2. The biological bath 2 is in contact with the surrounding sewage 5 through this opening 12.

A suction pump of the positive displacement type 13 attached to the reaction vessel 1 and located in the probe base 4 serves as the proportioning device for the introduction of the sewage sample. In the execution model shown, this suction pump 13 incorporates a suction piston 14 whose cylinder 15 is connected to the reaction vessel 1. Power is provided to the suction pump by an electric motor 16 which is supplied with current by the control device 9.

A measurement cycle runs, for example, as follows. The growth bodies 3 are kept in turbulent motion in the biological bath 2 by the agitator 6. Each measurement cycle begins with the rinsing of the reaction vessel 1 with oxygen-saturated and moderated tap water by means of the opening of valve 11. The tap water then flows into the upper part of the reaction vessel 1. The water already inside leaves the reaction vessel 1 through the opening 12 in the lower part of the reaction vessel 1.

When the rinsing process is completed and the water mixture in the reaction vessel 1 from the previous measurement cycle has been replaced, a constant, predetermined amount of sewage is sucked through the opening 12 into the reaction vessel 1 by means of an upward movement of the suction piston 14. Because of the introduction of sewage there arises in the biological bath 2 a nutrient mixture consisting of dilution water and sewage which serves as the nutrient base for the bio-mass. The suction piston 14 returns to its lower initial position, in order to prevent the interior of the cylinder 15 from containing an unsatisfactorily mixed amount of fluid. In place of a suction piston 14 a positive displacement piston can also be used.

The degree of dilution, i.e., the relationship between the amount of sewage sample sucked in and the volume of the reaction vessel 1, is so selected, that the BOD concentration of the mixture lies in a range in which a largely linear relationship exists between the BOD concentration and the amount of oxygen breathed by the bio-mass. This relationship is known from the so-called Michaelis equation which was described in EP-B 0 049 887.

The constant degree of dilution and the resultant oxygen consumption per unit of time, which was determined by the oxygen concentration measured by the oxygen probe 8, are furnished to an evaluation computer in the central control device 9 for the determination of the biological oxygen demand. The determined level of BOD is displayed on an indicator device and registered.

After completion of the measurement the reaction vessel 1 is rinsed in the manner previously described by the introduction of dilution water through the line 10. The reaction vessel 1 is thereafter ready for another measurement cycle. The measuring thus occurs intermittently in a batch procedure.

Another possibility for calculating the BOD consists of so selecting the amount of the sewage sample sucked in, that the BOD composition of the mixture remains basically constant during each measurement cycle. In the process, then, the previous measurement is used to correct the following measurement. The oxygen consumption of the organisms must be kept constant in the process and serves as a guide value. Here the suction pump 13 is configured as an adjustable dosing pump, whereby, for example, a stroke control of the suction piston 14 is used.

The BOD is determined from the currently selected degree of dilution by means of an evaluation computer in the control unit 9.

By the use of additional measurement probes of the same type construction the toxicity of the sewage could simultaneously be measured in addition to the BOD. To do that the first measurement probe is operated in the manner described above to determine the BOD. With regard to the second measurement probe a basically greater amount of sewage is sucked into the reaction vessel 1 during each measurement cycle, in order to achieve so low a degree of dilution, that maximum oxygen consumption occurs by the bio-mass, in so far as no toxicity is present in the sewage. In the process the degree of dilution in the first measurement probe is always selected so large, that if there is toxicity in the sewage, there will be no influence on the measurement results of the measuring probe because of the toxicity. On the other hand the degree of dilution in the second measurement probe is always selected so high, that any toxicity present in the sewage has a negative effect. The BOD concentration of the mixture of sewage and dilution water in the second measuring probe is purposefully selected at least five times greater than in the first measuring probe. If both measuring probes show the same BOD value of the sewage, then no toxicity is present. A difference in the two measured BOD values shows the degree of toxicity.

The oxygen consumption in a constant sewage biology for normal communal sewage in relation to the BOD is almost linear until approx. 25 mg/l. For example in the measurement probe described to determine the BOD with a volume of 200 ml and a BOD concentration, $X_m$, of 25 mg/l, an oxygen consumption, $Y_m$, of about 1 mg O2/min would appear. For a limited time when the BOD concentration was approaching zero, an oxygen consumption, $Y_o$, of about 0.12 mg O2/min would appear as base breathing. There thus results a linear equation of the form:

$$Y = Y_{o+m}X$$

Y=O2 consumption in mg/min of a biology of 0–25 mg BOD/l. $Y_o$ is thereby the base breathing value of 0.12 mg O2/min.

The constant, m, thus results for the linear equation:

$$m = Y_m - Y_o/X_m = 1.0 - 0.12/24 = 0.035 \text{ mg O2min/mg BOD/l}$$

There thus results the BOD concentration $X_m$=25 mg BOD/l.

For a constant sewage-dilution water ratio of 1:20 the BOD measuring probe will determine a BOD concentration of 0–500 mg/l. The BOD is calculated as follows:

$$BOD = Y - Y_o/m(1+n),$$

whereby n is the portion of dilution water.

Example with numbers:

$$Y = 0.72 \text{ mg O2/min}$$

$$BOD = 0.72 - 0.12/0.035 + (1+19) = 342.8 \text{ mg BOD/l}$$

Process and device for determining the biological oxygen demand of sewage.

What is claimed is:

1. Process for determining a biological oxygen demand of sewage, whereby a sewage sample is mixed with biologically neutral dilution water at a predetermined degree of dilution, and in a biological bath an oxygen concentration present due to a biological reaction of a quantity of bio-mass with the diluted sewage sample in the biological bath is measured, the improvement comprising introducing from a first source a predetermined amount of the sewage sample into the biological bath filled with oxygen-saturated dilution water, measuring the resultant oxygen consumption per unit of time, and rinsing the biological bath with biologically neutral dilution water received from a second source separate from the first source.

2. Process according to claim 1 wherein a constant degree of dilution is regulated in the biological bath during each measurement cycle by means of the introduction of a constant amount of a sewage sample, and the biological oxygen demand being determined from the resultant oxygen consumption per unit of time.

3. Process according to claim 1, wherein the amount of sewage sample introduced during each cycle being so proportioned, that a constant, predetermined oxygen consumption per unit of time occurs in the biological bath, and the biological oxygen demand being determined from a currently selected degree of dilution.

4. Apparatus for determining a biological oxygen demand of sewage, comprising a reaction vessel adapted to receive a biological bath, a dosing device for introducing a sewage sample, an introductory device for introducing biologically neutral dilution water, and a device for determining an oxygen concentration in the biological bath, the improvement including a source of dilution water, and a feed line communicating therewith, the reaction vessel comprises a closed container into which the feed line for the dilution water empties, the device to determine the oxygen concentration including an oxygen probe placed in the reaction vessel, and the reaction vessel being in contact with the sewage to be evaluated by means of an opening which defines both a feeder opening for the sewage sample and an exhaust opening for the rinsing of the biological bath, the closed container including a wall disposed opposite to, and facing, the opening, the wall being immobile.

5. Device according to claim 4 wherein the reaction vessel forms a probe head adapted to be immersed in the sewage sample to be evaluated.

6. Device according to claim 5 wherein the dosing device for the sewage sample comprises a positive displacement type suction pump attached to the reaction vessel.

7. Device according to claim 6 wherein the suction pump includes a piston disposed in a cylinder connected to the reaction vessel.

8. Device according to claim 6, further including an agitator extends into the reaction vessel for agitating the biological bath.

9. Device according to claim 8 wherein the oxygen probe, the suction pump, and the agitator are combined in a probe base on which the reaction vessel is attached in the form of a probe head.

* * * * *